(12) United States Patent
Kawai et al.

(10) Patent No.: US 7,628,938 B2
(45) Date of Patent: Dec. 8, 2009

(54) PHOTOCHROMIC COMPOUND AND OPTICAL FUNCTIONAL MATERIAL

(75) Inventors: Tsuyoshi Kawai, Ikoma (JP); Takuya Nakajima, Ikoma (JP); Shigekazu Kawai, Ikoma (JP)

(73) Assignee: National University Corporation Nara Institute of Science and Technology, Ikoma-shi (JP)

( * ) Notice: Subject to any disclaimer, the term of this patent is extended or adjusted under 35 U.S.C. 154(b) by 14 days.

(21) Appl. No.: 11/723,668

(22) Filed: Mar. 21, 2007

(65) Prior Publication Data

US 2008/0006797 A1 Jan. 10, 2008

(30) Foreign Application Priority Data

Jul. 10, 2006 (JP) ............................. 2006-189651

(51) Int. Cl.
*G02B 5/23* (2006.01)
(52) U.S. Cl. .................... 252/586; 548/148; 548/202; 548/235; 548/335.1; 548/563; 548/564; 549/83; 585/16; 585/24
(58) Field of Classification Search ................ 252/586; 548/148, 202, 235, 335.1, 563, 564; 549/83; 585/16, 24
See application file for complete search history.

(56) References Cited

FOREIGN PATENT DOCUMENTS

CN 1530365 * 9/2004
JP A-2005-325087 11/2005

OTHER PUBLICATIONS

Tsuyoshi Kawai, Taisuke Iseda and Masahiro Irie, Photochromism of triangle terthiophene derivatives as molecular re-router, Chem. Commun., 2004, 72-73. The manuscript is published by The Royal Society of Chemistry 2004.*

Tsuyoshi Kawai, Taisuke Iseda and Masahiro Irie, Photochromism of triangle terthiophene derivatives as molecular re-router, Chem. Commun., 2004, 72-73, The Royal Society of Chemistry 2004.*

* cited by examiner

*Primary Examiner*—Harold Pyon
*Assistant Examiner*—Bijan Ahvazi
(74) *Attorney, Agent, or Firm*—Oliff & Berridge, PLC

(57) ABSTRACT

The present invention provides a photochromic compound that is colored when irradiated with visible light and quickly faded when set in a dark place. The photochromic compound according to the present invention is expressed by the following general formula (I):

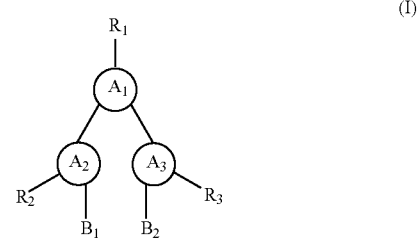

(I)

where each of $A_1$, $A_2$ and $A_3$ is a five-member rings forming a 6π-electron system, the three rings being identical, partially identical or totally different from each other, and each ring may have a substituent; $B_1$ and $B_2$ are functional groups, each having an atomic number of five or larger, including a ring compound, and bonded to the 2-carbon of each of $A_2$ and $A_3$, respectively; and $R_1$, $R_2$ and $R_3$ are substituents identical to or different from each other. This compound is highly colorable and durable even when it is dispersed into plastic macromolecular materials. Therefore, it is suitable as a dye material for sunglasses or similar products.

8 Claims, 7 Drawing Sheets

TA-1a
TA-2a
TA-3a
TA-4a

TA-1b
TA-2b
TA-3b
TA-4b (1) → (2)

(3) → (TA-1a)

Fig. 6
| | RING-OPENED<br>a max(nm) | RING-CLOSED<br>b max(nm) | $E_a$ (kJmol$^{-1}$) | $A \times 10^{11}$ (S$^{-1}$) |
|---|---|---|---|---|
| TA-1 | 266 ($\varepsilon = 3.47 \times 10^4$) | 600 ($\varepsilon = 0.938 \times 10^4$) | 91.6 | 0.0477 |
| TA-2 | 333 ($\varepsilon = 4.00 \times 10^4$) | 637 | 82.9 | 1.37 |
| TA-3 | 328 ($\varepsilon = 3.30 \times 10^4$) | 610 | 90.6 | 17.6 |
| TA-4 | 329 ($\varepsilon = 4.52 \times 10^4$) | 648 | 83.3 | 927 |
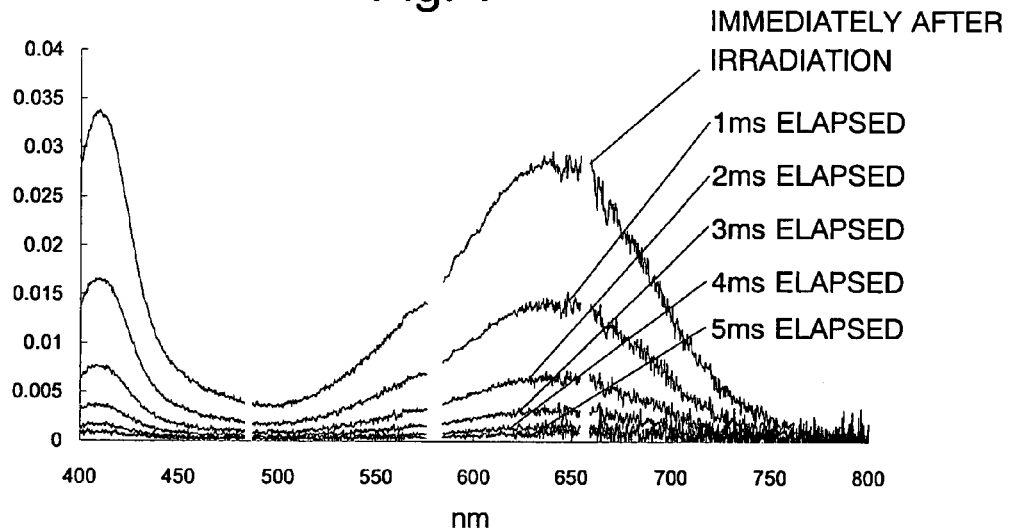
Fig. 7
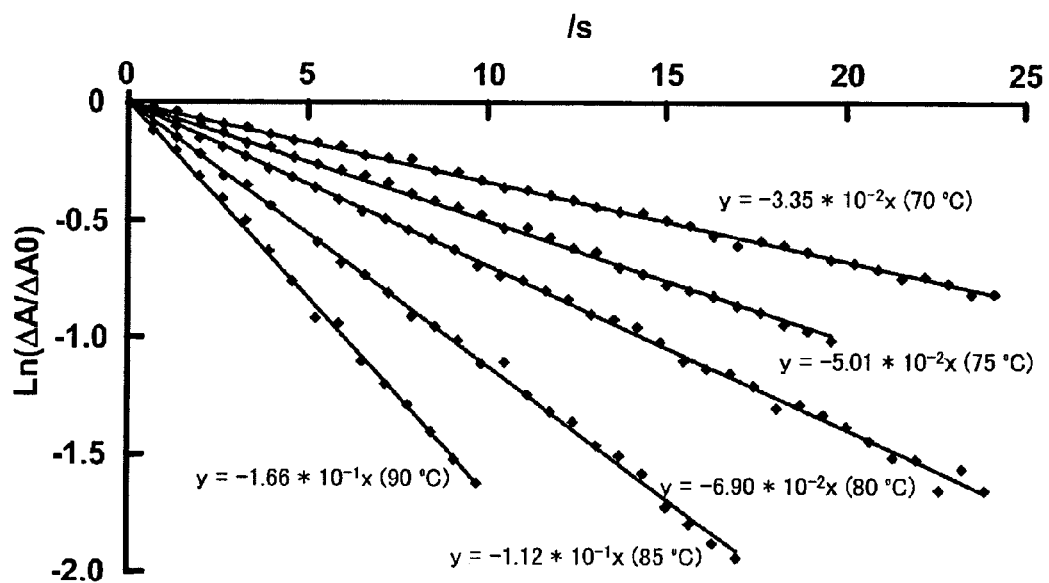
Fig. 8

(a) BEFORE IRRADIATION  (b) IMMEDIATELY AFTER IRRADIATION  (c) 10sec ELAPSED  (d) 30sec ELAPSED

PHOTOCHROMIC COMPOUND AND OPTICAL FUNCTIONAL MATERIAL

The present invention relates to a photochromic compound. Particularly, it relates to a photochromic compound that allows fast thermal fading rate.

BACKGROUND OF THE INVENTION

Photochromic substances are such materials whose molecules reversibly isomerized when they are irradiated with light.

One of the photochromic substances conventionally studied by many people is diarylethene. FIG. 15 shows the structural formula of a diarylethene molecule. Diarylethene turns to a colored state when it is irradiated with ultraviolet light and to a faded state (i.e. the original state) when it is irradiated with visible light. In addition to this photochromic property, diarylethene has the following characteristics:

It has a high quantum yield. That is, it is quick to change its color and highly colorable.

It is very reactive when it is in a polymer. Therefore, it can be easily fused with various materials.

It is durable. The coloring and fading properties scarcely deteriorate even after the coloring and fading reactions are repeated ten thousand times.

It is thermally stable. Its half-life from the colored state to the faded state is approximately 2000 years.

Due to these characteristics, diarylethene is suitable for application to optical recording materials and there are various research and development activities underway, aiming at its practical use. For example, Japanese Unexamined Patent Application Publication No. 2005-325087 discloses an optical functional device employing multiphoton absorption using diarylethene compounds.

As stated previously, diarylethene is thermally very stable. In other words, it is very slow to be thermally faded. This means it will virtually never undergo natural fading.

If diarylethene or a similar photochromic substance having a high quantum yield, high durability and high thermal stability has a higher thermo-fading speed, the substance will have greater possibilities as dimmer materials for sunglasses and other products.

Efforts have been made for researching a photochromic substance having a higher thermo-fading speed. One example is silver salt, which is used as a material for sunglasses that become colored when they are irradiated with visible light. However, silver salt can be used only for glass. In recent years, with the increasing use of plastics as industrial materials, organic photochromic substances have been demanded. Candidates of such substances include photochromic molecules of a spironaphtooxazine group. However, this substance is low in colorability and weak on durability.

On the other hand, it has been also attempted to provide a derivative of diarylethene with thermo-fadability. It is known that introduction of a branched alkoxy group as a substituent shortens the thermo-fading time of the derivative to approximately 20 seconds. From practical viewpoints, however, the period of 20 seconds is still too long as the thermo-fading time. For example, this photochromic compound is unsuitable for sunglasses because wearing such sunglasses will be dangerous for car drivers, especially when the car is on a road with many tunnels. Moreover, fading this compound requires a temperature of 100 degrees Celsius or even higher, which is impractical. Any photochromic substance to be used in sunglasses or visors under normal conditions must have a thermo-fading time shorter than 10 seconds at room temperature.

SUMMARY OF THE INVENTION

An objective of the present invention is to provide a photochromic compound having an improved thermo-fading speed while maintaining the advantageous photochromic properties due to the diarylethene skeleton.

The photochromic compound according to the present invention is expressed by the following general formula:

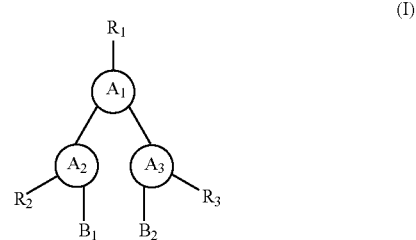

(I)

where:

each of $A_1$, $A_2$ and $A_3$ is a five-member ring forming a $6\pi$-electron system, the three rings being identical, partially identical or totally different from each other, and each ring may have a substituent;

$B_1$ and $B_2$ are functional groups identical to or different from each other, each group having an atomic number of five or larger, including a ring compound, and bonded to the 2-carbon of each of $A_2$ and $A_3$, respectively; and $R_1$, $R_2$ and $R_3$ are substituents identical to or different from each other.

Preferably, each of $A_1$, $A_2$ and $A_3$ in the general formula (I) is one of the following substances: thiazole, thiophene, pyrrole, indole, oxazole, imidazole and imidazolium. Preferably, one or both of $B_1$ and $B_2$ in the general formula (I) should be phenylethynyl.

In a preferable mode of the present invention, the photochromic compound includes thiazole as $A_1$, thiophene as $A_2$ and $A_3$, and phenylethynyl as $B_1$ and $B_2$ in the general formula (I).

In a preferable mode of the present invention, the photochromic compound is expressed by the following structural formula:

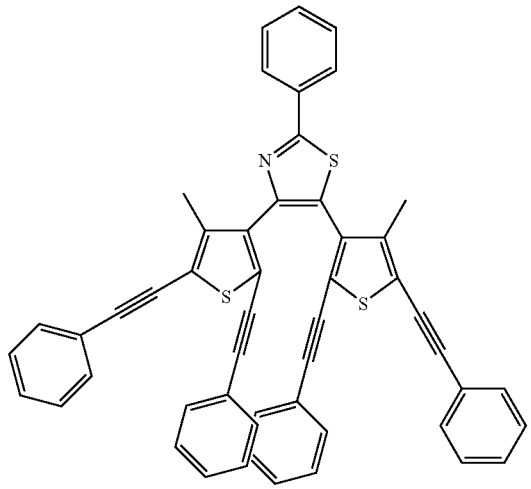

which is a variation of the general formula (I) and includes thiazole as $A_1$, thiophene as $A_2$ and $A_3$, phenyl as $R_1$, and phenylethynyl as $R_2$, $R_3$, $B_1$ and $B_2$.

The photochromic compound according to the present invention described thus far has a high quantum yield and is quick to be thermally faded. It can be faded with visible light and is highly dispersible into plastic macromolecular materials. Therefore, the present photochromic compound is suitable as optical functional materials for high-response dimming devices, such as sunglasses or visors for car drivers.

BEST MODES FOR CARRYING OUT THE INVENTION

To improve the thermo-fading speed, the present inventors have designed the molecule as follows: In general, to improve the thermo-fading speed, two factors relating to the molecular design need to be controlled. For example, suppose the speed is defined by the Arrhenius equation: $k=A\exp(-E/RT)$, where A is the frequency factor, E is the activation energy, R is the gas constant and T is the absolute temperature. In this case, one requirement is to lower the activation energy E and the other is to raise the frequency factor A.

To lower the activation energy E of the thermo-fading reaction, it is necessary to improve the stability of the ring-opened form (i.e. uncolored state) of the photochromic compound to make the ring-closed form relatively unstable. Adding a conjugated molecule to the 2-carbon of each of $A_2$ and $A_3$ is effective in lowering the activation energy E. Adding the conjugated molecules makes the ring-opened form more stable due to resonance stabilization energy. However, it cannot stabilize the ring-closed form because the compound in this form has sp3 hybrid orbitals.

To enhance the frequency factor, a preferable technique is to locate a C—C bond that must be broken open to change the compound from the ring-closed form to the ring-opened form and optimize the surroundings of that C—C bond so that thermal energy can concentrate on it.

The photochromic compound according to the present invention satisfies the above conditions and has the following general formula (I):

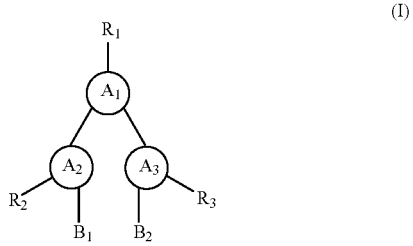

(I)

In the general formula (I), each of $A_1$, $A_2$ and $A_3$ is a five-member ring forming a 6π-electron system. The three systems may be identical, partially identical or totally different from each other. $A_1$, $A_2$ and $A_3$ may have any structures as long as those structures are photochromically reactive. Examples include thiazole, thiophene, pyrrole, indole, oxazole, imidazole and imidazolium. The five-member ring of $A_1$, $A_2$ or $A_3$ may have a condensed ring, such as benzothiophene or indole. Each of the three rings may have one or more substituents; the substituent may be located at the condensed ring.

In the general formula (I), $B_1$ and $B_2$ are functional groups identical to or different from each other, each group having an atomic number of five or larger, including a ring compound, and bonded to the 2-carbon of each of $A_2$ and $A_3$, respectively. For the reason explained previously, $B_1$ and $B_2$ should be preferably π-conjugated substituents. Furthermore, $B_1$ and $B_2$ should preferably have a rigid molecular frame including, for example, a triple bond. This condition improves the frequency factor and thereby enhances the thermo-fading speed.

In the photochromic compound according to the present invention, any substance that satisfies the above requirements can be used as $B_1$ or $B_2$. Especially preferable examples are methyl, phenylethynyl, thiophene, phenylenevinylene and thienylenevinylene. The phenylethynyl group is particularly suitable.

The photochromic compound according to the present invention expressed by the general formula (I) becomes an isomer having the structure expressed by the following general formula (II) when it is irradiated with light:

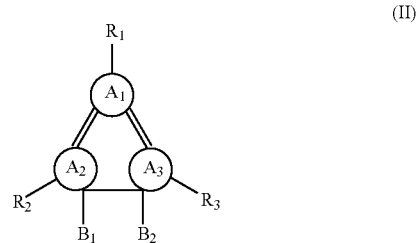

(II)

The compound expressed by the general formula (II) is unstable for the reason explained earlier. Though it retains the colored state while it is being irradiated with light, the compound naturally returns to the faded state expressed by the general formula (I) after the irradiation is discontinued.

In the photochromic compound according to the present invention, the color of the compound in the colored state, i.e. the light absorption characteristics of the compound expressed by the general formula (II), can be regulated by the choice of $R_1$ in the general formula (I) (or (II)). Accordingly, in the photochromic compound according to the present invention, the structure of $R_1$ should not be limited; it is preferable to choose the structure according to the intended use of the compound. However, it should be noted that use of a substituent having many π-conjugate electrons will make the compound highly colorable. Examples of $R_1$ include phenyl, thiophene, naphthyl and other aryl groups, and alkyl groups. Oligothiophene and phenylenevinylene are also available.

$R_2$ and $R_3$ may be identical to or different from each other. They are bonded to the carbon atom at the α-position of $A_2$ and $A_3$, except the carbon at the reaction site. The photochromic compound according to the present invention changes its color in the colored state when $R_2$ or $R_3$ is replaced with a different functional group. Accordingly, none of $R_2$ and $R_3$ should be limited to specific functional groups. However, it should be noted that using a group having many π-conjugated electrons as $R_2$ or $R_3$ will lower the quantum yield of the fading reaction caused by visible light and thereby improve the colorability. Examples of the functional groups available as $R_1$ or $R_2$ in the present invention include phenylethynyl, thiophene, phenylenevinylene and thienylenevinylene.

BRIEF DESCRIPTION OF THE DRAWINGS

FIG. 6 is a table showing the difference of the light absorption characteristic between the opened and ring-closed forms of photochromic compounds according to the present invention.

FIG. 7 is a graph showing the absorption spectrum measured at intervals of 1 millisecond during the process of isomerization from TA-4b into TA-4a.

FIG. 8 is a graph showing the temporal change of the absorbance during the process of isomerization from TA-2b into TA-2a and its temperature dependency.

EXAMPLES

Figure 1:
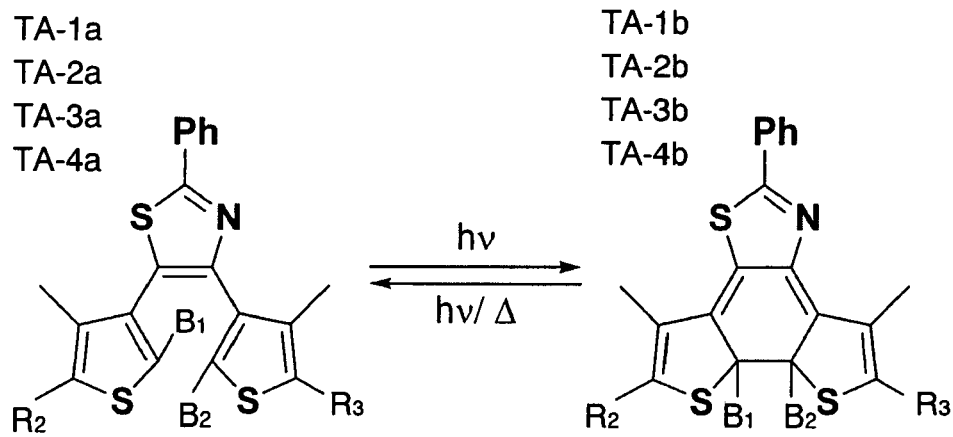
FIG. 1 shows an example of the photochromic compound according to the present invention.

Four compounds (TA-1a, TA-2a, TA-3a and TA-4a) as shown in FIG. 1, all expressed by the general formulas (I) and (II) have been prepared, including phenyl as $R_1$, thiazole as $A_1$ and thiophene as $A_2$ and $A_3$, to examine and compare their characteristics. Each compounds contained the substituents $B_1$, $B_2$, $R_2$, and $R_3$ as follows:

TA-1a ... $B_1$ and $B_2$: methyl, $B_1$ and $B_2$: phenyl.
TA-2a ... $B_1$: methyl, $B_2$: phenylethynyl, $R_2$: phenyl, $R_3$: phenylethynyl
TA-3a ... $B_1$: phenylethynyl, $B_2$: methyl, $R_2$: phenylethynyl, $R_3$: phenyl
TA-4a ... $B_1$, $B_2$, $R_2$ and $R_3$: phenylethynyl The compounds TA-1a through TA-4a were synthesized by Suzuki-Miyaura coupling reactions of a dibromo-form of $A_1$ and boron derivatives of $A_2$ and $A_3$ under the catalytic influence of palladium. The reaction of producing TA-3 and TA-2, which were bilaterally asymmetrical, was conducted in steps taking into account the fact that thiazole is more reactive at the 5-carbon than at the 4-carbon.

Figure 2:
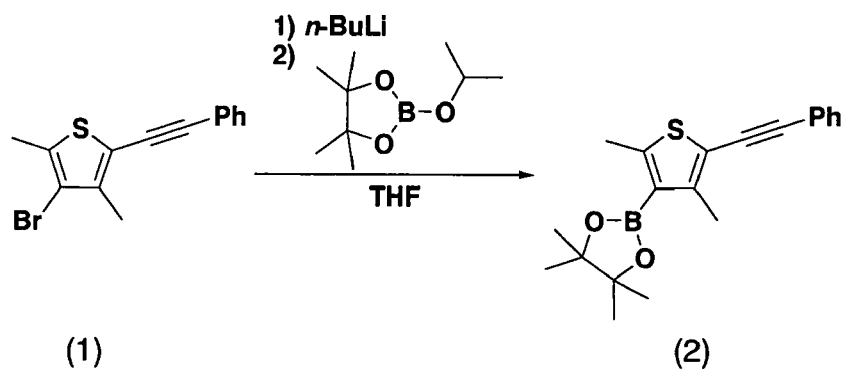
FIG. 2 shows a method of creating Ta-1a as an example of the photochromic compound according to the present invention.
Figure 2:
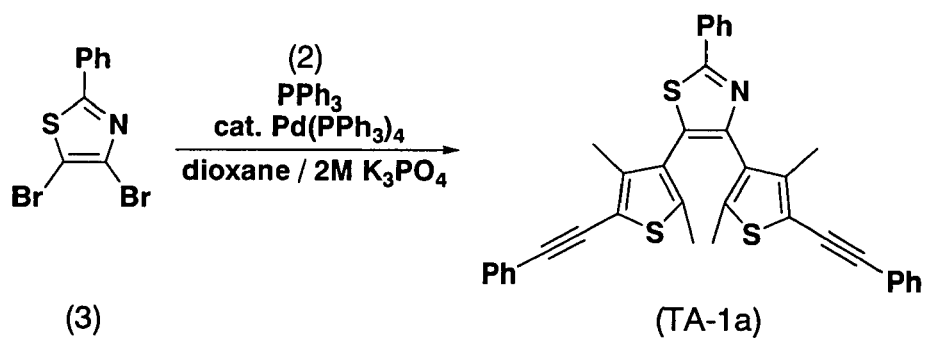

Referring to FIG. 2, the method of synthesizing TA-1a is described:

A reactor system including a 300 ml four-necked flask with a dropping funnel and a three-way cock was flame dried and the air inside was replaced with argon gas. Into this reactor, 100 ml of dehydrated tetrahydrofuran was introduced to prepare a solution of the partially purified compound (1) (ca. 32 mmol). Then, the solution was cooled to −78 degrees Celsius with methanol/$N_2$. Into this solution, a hexane solution of n-buthyllithium (20 ml, 32 mmol) was slowly released, with the temperature maintained. After the releasing was completed, the solution was stirred for one hour, with the same temperature maintained. Then, 2-isopropoxy-4,4,5,5-tetramethyl-1,3,2-dioxaborolane (6.5 ml, 32 mmol) was released into it, with the temperature still maintained. After this releasing process was completed, the solution was heated to room temperature and stirred for one day. After the reaction was completed, the reaction solution was neutralized with diluted hydrochloric acid. The neutralized solution was extracted three times with ethyl acetate, and its organic layer was cleansed with saturated saline. The organic layer was dried with $MgSO_4$, and the solvent was distilled away. The partially purified product (2) thus obtained was maintained in the mixed state and used in the next reaction.

Next, the compound (3) (3.21 g, 1.01 mmol), the partially purified compound (2), and $PPh_3$ (2.65 g, 10.1 mmol) were put into a 100 ml recovery flask (eggplant flask), and they were dissolved into a mixture of 100 ml of 2M $K_3PO_4$ and 100 ml of dioxane. After $N_2$ bubbling was carried out for 10 minutes, $Pd(PPh_3)_4$ (570 mg, 0.493 mmol) was added and the solution was heated and stirred for 72 hours at 110 degrees Celsius. After the reaction was completed, the reaction solution was separated three times with ethyl acetate, and the organic layer thereby created was cleansed with saturated saline. The organic layer was dried with $MgSO_4$, and the solvent was distilled away. The partially purified product thus obtained was separated by silica gel column chromatography (hexane:AcOEt=15:1) and then fully purified by normal phase high performance liquid chromatography (HPLC) and reversed phase HPLC to obtain a white solid, i.e. TA-1a. The amount obtained was 50 mg (0.0859 mmol) and the yield was 0.85%.

Figure 3:
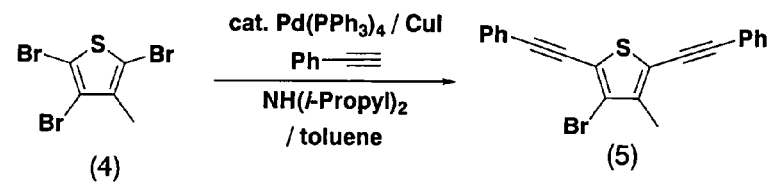
FIG. 3 shows a method of creating Ta-2a as an example of the photochromic compound according to the present invention.
Figure 3:
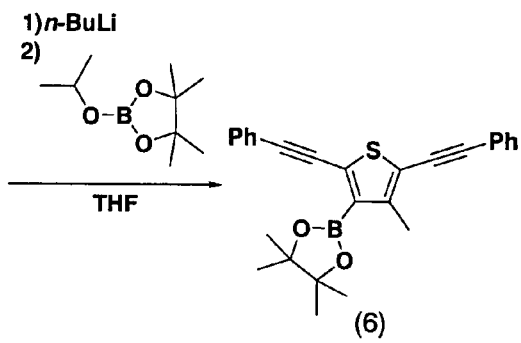
Figure 3:
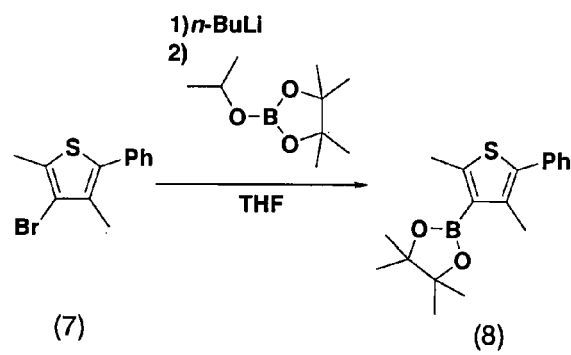
Figure 3:
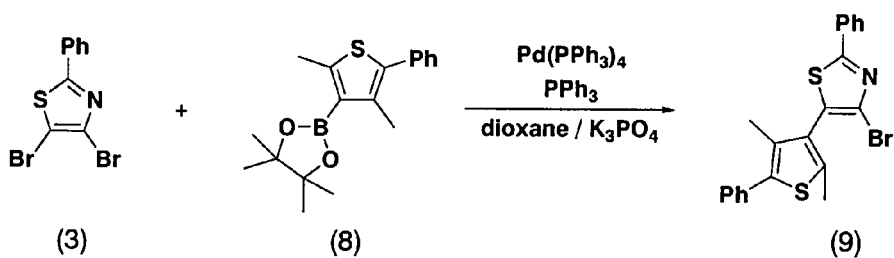
Figure 3:
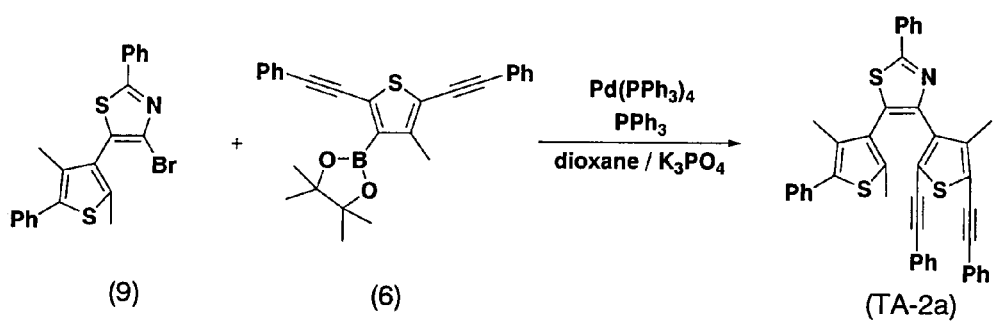

Referring to FIG. 3, the method of synthesizing TA-2a is described:

The compound (4) (20 g, 60 mmol) and phenylacetylene (14 ml, 170 ml) were dissolved into a cosolvent of 300 ml of di-isopropylamine and 180 ml of toluene, and $N_2$ bubbling was carried out for 10 minutes. Then, $Pd(PPh_3)_4$ (1.5 g, 1.3 mmol) and CuI (230 mg, 12 mmol) were added and the solution was stirred for 12 hours at 50 degrees Celsius. After the reaction was completed, the resultant mixture was extracted three times with ethyl acetate, and its organic layer was cleansed with saturated saline. The organic layer was dried with $MgSO_4$, and the solvent was distilled away. The partially purified substance thus obtained was purified by silica gel column chromatography (hexane:AcOEt=10:1) to obtain a yellow crystal, i.e. the compound (5).

Next, a reactor system including a 1000 ml four-necked flask with a dropping funnel and a three-way cock was flame dried and the air inside was replaced with argon gas. Into this reactor, 400 ml of dehydrated tetrahydrofuran was introduced to prepare a solution of the compound (5) (7.55 g, 20.0 mmol). Then, the solution was cooled to −78 degrees Celsius with methanol/$N_2$. Into this solution, a hexane solution of n-buthyllithium (13.8 ml, 22 mmol, 1.1 eq.) was slowly released, with the temperature maintained. After the releasing was completed, the solution was stirred for one hour, with the same temperature maintained. Then, 2-isopropoxy-4,4,5,5-tetramethyl-1,3,2-dioxaborolane (6.5 ml, 32 mmol) was released into it, with the temperature still maintained. After this releasing process was completed, the solution was heated to room temperature and stirred for one day. After the reaction was completed, the reaction solution was neutralized with diluted hydrochloric acid. The neutralized solution was extracted three times with ethyl acetate, and its organic layer was cleansed with saturated saline. The organic layer was dried with $MgSO_4$, and the solvent was distilled away. The partially purified substance thus obtained was recrystalized with ethanol to obtain the compound (6).

On the other hand, a reactor system including a 300 ml four-necked flask with a dropping funnel and a three-way cock was flame dried and the air inside was replaced with argon gas. Into this reactor, 150 ml of dehydrated tetrahydrofuran was introduced to prepare a solution of the compound (7) (2.55 g, 10.0 mmol). Then, the solution was cooled to −78 degrees Celsius with methanol/$N_2$. Into this solution, a hexane solution of n-buthyllithium (6.9 ml, 11.0 mmol, 1.1 eq.) was slowly released, with the temperature maintained. After the releasing was completed, the solution was stirred for one hour, with the same temperature maintained. Then, 2-isopropoxy-4,4,5,5-tetramethyl-1,3,2-dioxaborolane (2.4 ml, 11.8 mmol) was released into it, with the temperature still maintained. After this releasing process was completed, the solution was heated to room temperature and stirred for one day. After the reaction was completed, the reaction solution was neutralized with diluted hydrochloric acid. The neutralized solution was extracted three times with ethyl acetate, and its organic layer was cleansed with saturated saline. The organic layer was dried with $MgSO_4$, and the solvent was distilled away. The partially purified substance thus obtained was recrystalized with ethanol to obtain the compound (8).

Furthermore, the compound (3) (314 mg, 0.984 mmol), the compound (8) (314 mg, 1.00 mmol), and $PPh_3$ (138 mg, 0.526 mmol) were put into a 100 ml recovery flask, and they were dissolved into a mixture of 20 ml of 2M $K_3PO_4$ and 20 ml of dioxane. After $N_2$ bubbling was carried out for 10 minutes, $Pd(PPh_3)_4$ (63 mg, 0.0545 mmol) was added and the solution was heated and stirred for three days at 90 degrees Celsius. After the reaction was completed, the reaction solution was separated three times with ethyl acetate, and the organic layer thereby created was cleansed with saturated saline. The organic layer was dried with $MgSO_4$, and the solvent was distilled away. The partially purified product thus obtained was separated by silica gel column chromatography (hexane:AcOEt=19:1) and then fully purified by HPLC to obtain a white solid, i.e. the compound (9).

The compound (9) (430 mg, 1.0 mmol), the compound (6) (424 mg, 1.0 mmol) and $PPh_3$ (40 mg, 0.15 mmol) were put into a 100 ml recovery flask and dissolved into a mixture of 15 ml of 2M $K_3PO_4$ and 35 ml of dioxane. After $N_2$ bubbling was carried out for 10 minutes, $Pd(PPh_3)_4$ (20 mg, 0.017 mmol) was added and the solution was heated and stirred for three days at 90 degrees Celsius. After the reaction was completed, the reaction solution was separated three times with ethyl acetate, and the organic layer thereby created was cleansed with saturated saline. The organic layer was dried with $MgSO_4$, and the solvent was distilled away. The partially purified product thus obtained was separated by silica gel column chromatography (hexane:AcOEt=19:1) and then fully purified by HPLC to obtain a white solid, i.e. TA-2a. The amount obtained was 469 mg and the yield was 73%.

Figure 4:
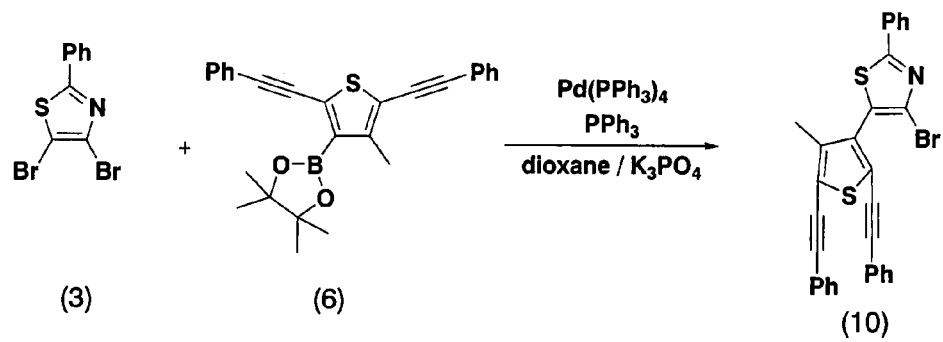
FIG. 4 shows a method of creating Ta-3a as an example of the photochromic compound according to the present invention.
Figure 4:
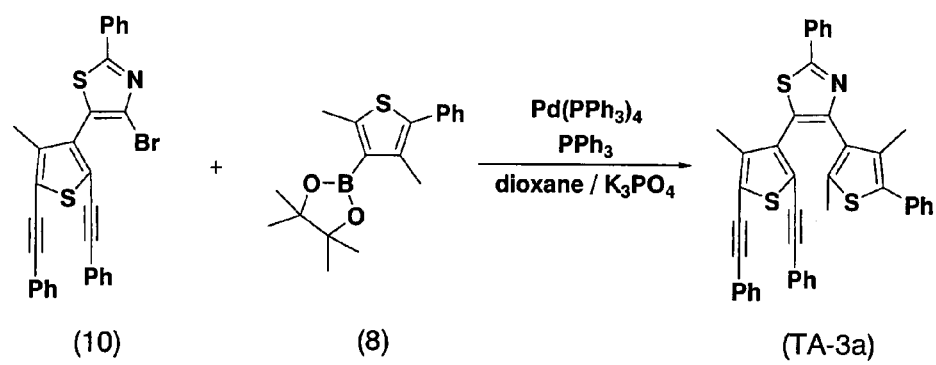

Referring to FIG. 4, the method of synthesizing TA-3a is described:

The compound (3) (316 mg, 0.991 mmol), the compound (6) (426 mg, 1.0 mmol) and $PPh_3$ (130 mg, 0.50 mmol) were put into a 100 ml recovery flask, and they were dissolved into a mixture of 40 ml of 2M $K_3PO_4$ and 85 ml of dioxane. After $N_2$ bubbling was carried out for 10 minutes, $Pd(PPh_3)_4$ (60 mg, 0.052 mmol) was added and the solution was heated and stirred for three days at 90 degrees Celsius. After the reaction was completed, the reaction solution was separated three times with ethyl acetate, and its organic layer was cleansed with saturated saline. The organic layer was dried with $MgSO_4$, and the solvent was distilled away. The partially purified product thus obtained was separated by silica gel column chromatography (hexane:AcOEt=19:1) and then fully purified by HPLC to obtain a white solid, i.e. the compound (10).

Next, the compound (10) (110 mg, 0.2 mmol), the compound (8) (60 mg, 0.19 mmol) and $PPh_3$ (23 mg, 0.088 mmol) were put into a 100 ml recovery flask and dissolved into a mixture of 15 ml of 2M $K_3PO_4$ and 15 ml of dioxane. After $N_2$ bubbling was carried out for 10 minutes, $Pd(PPh_3)_4$ (20 mg, 0.017 mmol) was added and the solution was heated and stirred for three days at 90 degrees Celsius. After the reaction was completed, the reaction solution was separated three times with ethyl acetate, and the organic layer thereby created was cleansed with saturated saline. The organic layer was dried with $MgSO_4$, and the solvent was distilled away. The partially purified product thus obtained was separated by silica gel column chromatography (hexane:AcOEt=19:1) and then fully purified by HPLC to obtain a white solid, i.e. TA-3a. The amount obtained was 10 mg and the yield was 8.2%.

Figure 5:
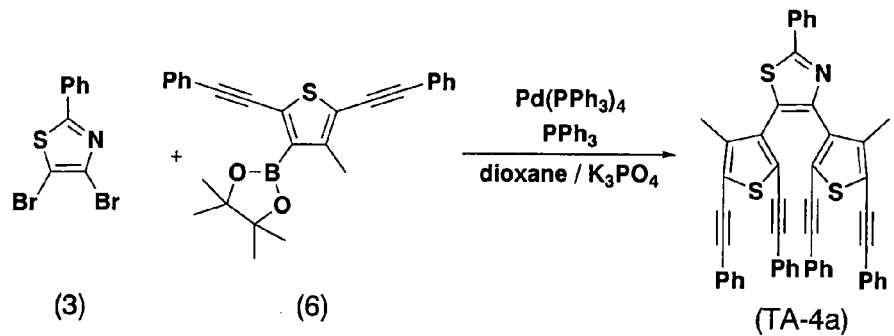
FIG. 5 shows a method of creating Ta-4a as an example of the photochromic compound according to the present invention.

Referring to FIG. 5, the method of synthesizing TA-4a is described:

The compound (3) (56 mg, 0.18 mmol), the compound (6) (150 mg, 0.35 mmol) and $PPh_3$ (25 mg, 0.095 mmol) were put into a 100 ml recovery flask, and they were dissolved into a mixture of 15 ml of 2M $K_3PO_4$ and 15 ml of dioxane. After $N_2$ bubbling was carried out for 10 minutes, $Pd(PPh_3)_4$ (20 mg, 0.017 mmol) was added and the solution was heated and stirred for three days at 90 degrees Celsius. After the reaction was completed, the reaction solution was extracted three times with ethyl acetate, and the organic layer thereby created was cleansed with saturated saline. The organic layer was dried with $MgSO_4$, and the solvent was distilled away. The partially purified product thus obtained was separated by silica gel column chromatography (hexane:AcOEt=19:1) and then fully purified by HPLC to obtain a light-yellow solid, i.e. TA-4a. The amount obtained was 15 mg and the yield was 11%.

The molecular structure of each of TA-1a, TA-2a, TA-3a and TA-4a were identified with $^1$H-NMR and a high-resolution mass spectrometer. When solutions of TA-1a, TA-2a, TA-3a and TA-4a were irradiated with ultraviolet light, the originally colorless solutions turned turquoise blue. Then, when irradiated with visible light, they returned to the colorless state. The molecules in the colored state, which have the ring-closed form, are referred to as TA-1b, TA-2b, TA-3b and TA-4b hereinafter, as shown on the right side of FIG. 1. An examination of the absorption spectrums of these compounds confirmed the occurrence of a reversible change at room temperature. Isosbestic points were observed, which confirmed that a reversible two-component isomerization took place.

FIG. 6 is a table showing the light absorption characteristics of the four compounds in the ring-closed forms (TA-1a, TA-2a, TA-3a and TA-4a) and in the ring-opened forms (TA-1b, TA-2b, TA-3b and TA-4b). This table shows that increasing the number of phenylethynyl groups incorporated into the compound will make the maximum wavelength λmax longer. The fact that the absorption band of TA-2b is longer than that of TA-3b suggests that the color will change depending on the length of the π-conjugated system.

TA-1b was stable in a dark place at room temperature. However, TA-2b, TA-3b and TA-4b returned to the colorless state: TA-2a, TA-3a and TA-4a even in the dark place. TA-4b was particularly unstable and immediately transformed to TA-4a immediately after it was brought back to room temperature. These results demonstrate that TA-2b, TA-3b and TA-4b will be faded in response to a temperature as well as an illumination change.

A nuclear magnetic resonance (NMR) spectrum of TA-4a measured at a low temperature of −25 degrees Celsius showed NMR peaks by a ratio of 1.1 (2.45 ppm):1.8 (2.05 ppm):1.9 (2.05 ppm):1.2 (1.88 ppm). These peaks, which resulted from the presence of methyl, disappeared when the temperature was changed from −25 through −10 to 0 degrees Celsius.

Figure 10:
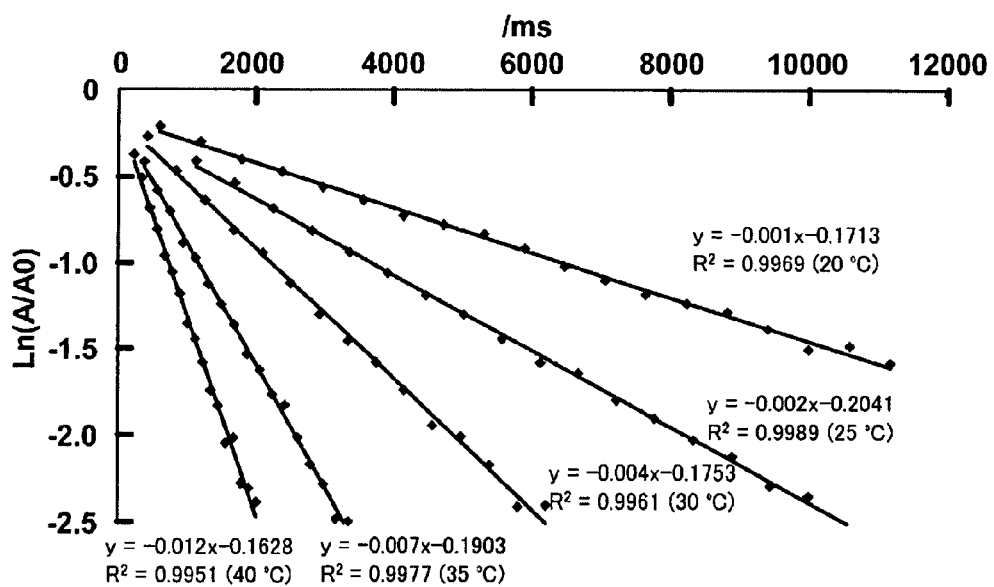
FIG. 10 is a graph showing the temporal change of the absorbance during the process of isomerization from TA-4b into TA-4a and its temperature dependency.

Next, the absorption spectrum of TA-4b was measured at intervals of 1 millisecond while it was returning (or isomerizing) to TA-4a. FIG. 7 shows the spectrum obtained, and FIG. 10 shows the temporal change of the absorbance measured at several temperatures. From FIG. 10, the first-order thermal ring-opening reaction constant k at 20 degrees Celsius can be calculated to be $0.135\ sec^{-1}$.

The half-life of TA-4b in the thermal ring-opening reaction was 7.0 seconds at 20 degrees Celsius, 1.8 seconds at 30 degrees Celsius, and 0.58 seconds at 40 degrees Celsius.

Figure 9:
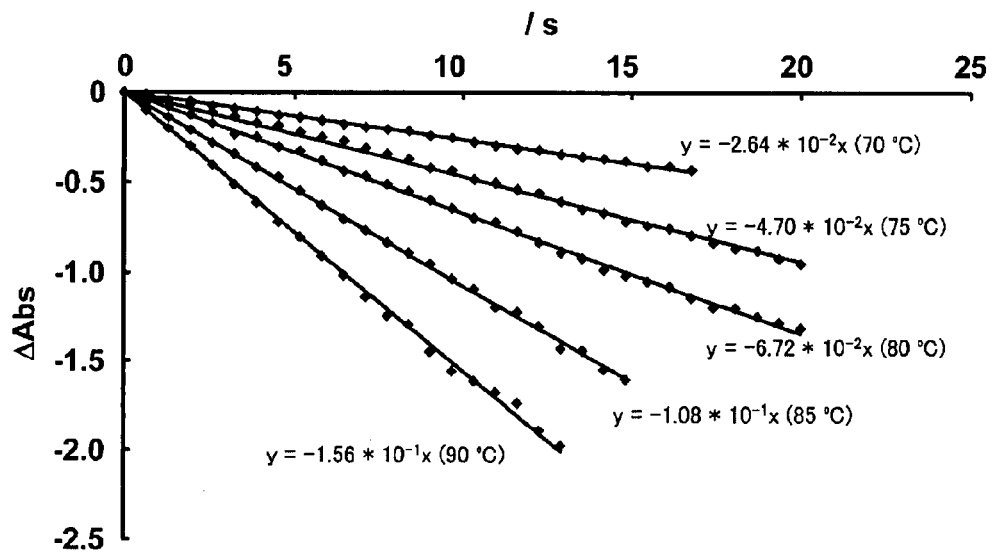
FIG. 9 is a graph showing the temporal change of the absorbance during the process of isomerization from TA-3b into TA-3a and its temperature dependency.

FIGS. 8 and 9 each show the temporal change of the absorbance of TA-2b or TA-3b at several temperatures during the process of isomerization from TA-2b or TA-3b to TA-2a or TA-3a. All these results indicate that the thermal fading speed of the photochromic compound according to the present invention can be controlled by appropriately selecting the substituents, particularly $R_2$, $R_3$, $B_1$ and $B_2$.

The table in FIG. 6 also shows the activation energy E and the frequency factor A of each compound. While the activation energy E changes by only a small amount, the frequency factor A significantly increases with the expansion of the α-conjugated system. As a result, the time constant of the thermal ring-opening reaction of TA-4 is much higher than those of TA-1 through TA-3. Thus, it has been proven that the introduction of phenylethynyl increases the thermo-fading speed of the compound.

Now, let us compare the thermo-fading speed of TA-4 with that of diarylethene. The thermodynamic parameters of diarylethene are $Ea=149\ kJmol^{-1}$ and $A=1.5\times10^{13}\ sec^{-1}$. From these values, its half-life can be estimated to be $0.153\times10^{13}$ seconds at 30 degrees Celsius. The half-life of TA-4, which was 1.8 seconds at 30 degrees Celsius, is about $10^{-11}$ of that of diarylethene. This proves that TA-4 has a remarkably high thermo-fading performance.

The present inventors also tested TA-4 under sunlight and found that the compound colored immediately after it had been irradiated with the sunlight. Then, when the compound was set under dark conditions, it quickly became transparent.

Comparative Example

Figure 11:
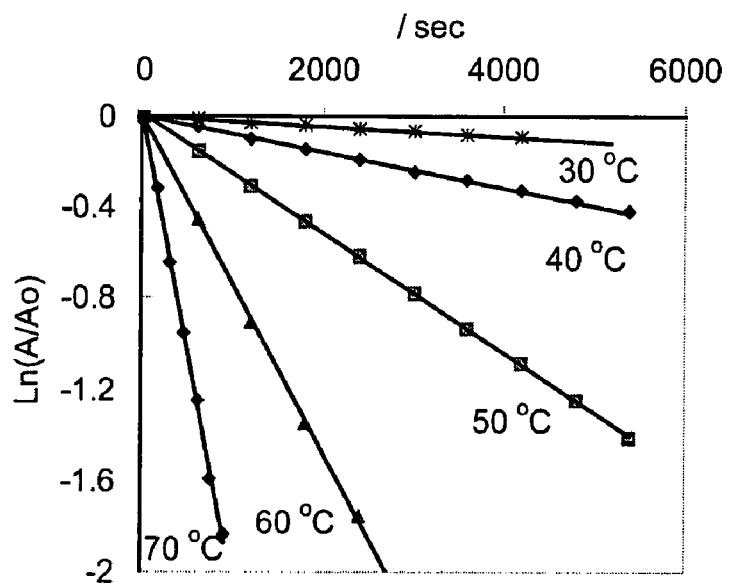
FIG. 11 is a graph showing the temporal change of the absorbance during the process of isomerization of Ta-A, a comparative example, and its temperature dependency.

A comparative example ("Ta-A") was prepared by incorporating methyl as both $B_1$ and $B_2$ and phenylethynyl as both $R_2$ and $R_3$ into the compound shown in FIG. 1. Then, the temporal change of its absorbance and its temperature dependency during the isomerization of Ta-A were examined. FIG. 11 shows the result. As can be seen from FIG. 11, Ta-A required several hours to be adequately thermo-faded at 30 degrees Celsius. This result also reinforces the previous conclusion that introduction of phenylethynyl as $B_1$ and $B_2$ is effective to create a photochromic compound having a short thermo-fading time.

Figure 12:
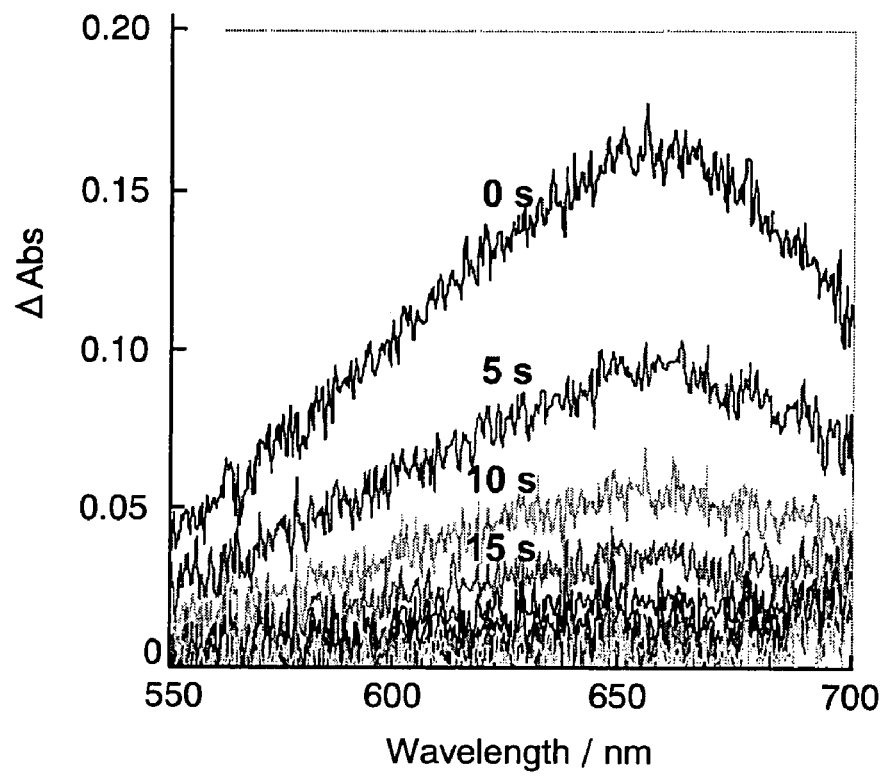
FIG. 12 is a graph showing the absorption spectrum measured at intervals of 5 seconds during the process of isomerization from TA-4a dispersed in polymethyl methacrylate (PMMA) to TA-4b.
Figure 13:
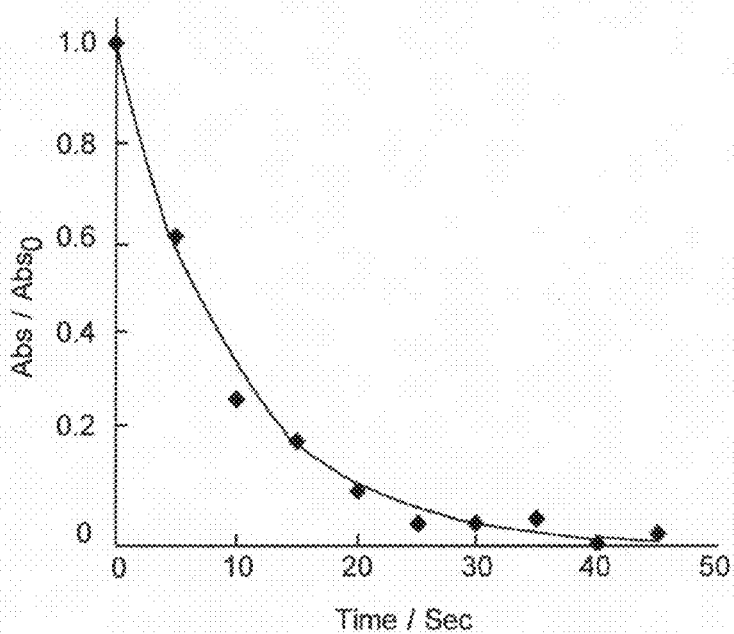
FIG. 13 is a graph showing the decay curve of the maximum absorption of PMMA in which Ta-4a is dispersed.
Figure 14:
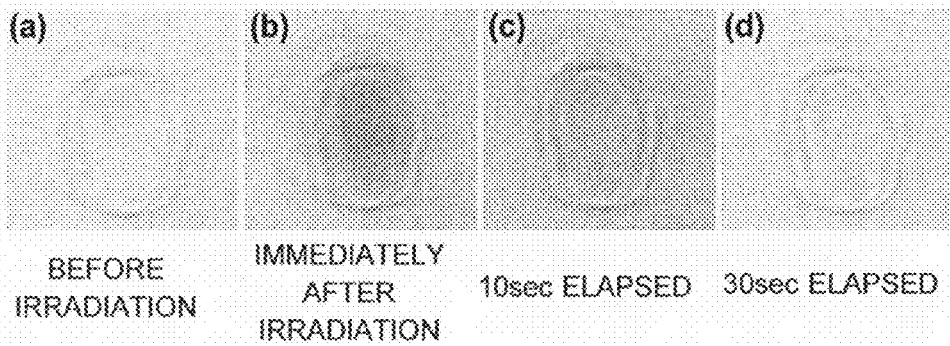
FIGS. 14(a) through 14(d) are pictures showing PMMA in which TA-4a was dispersed, taken (a) before an ultraviolet irradiation, (b) immediately after the ultraviolet irradiation, (c) 10 seconds and (d) 30 seconds after the ultraviolet irradiation.
Figure 15:
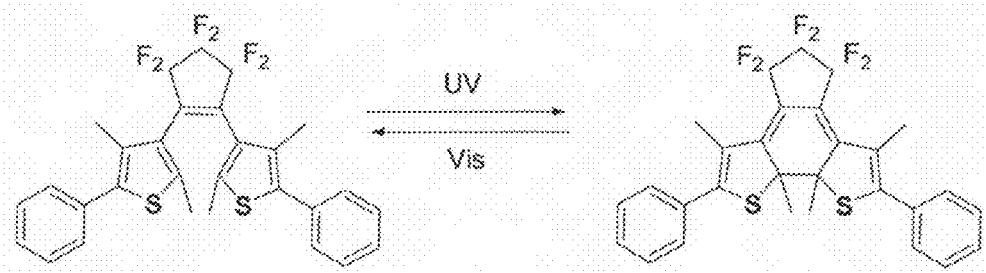
FIG. 15 is a structural formula of a diarylethene molecule.

Fading reaction in polymer:

TA-4a was dispersed into polymethyl methacrylate (PMMA), and its photo-fading reaction was examined at room temperature (20 degrees Celsius). FIG. 12 is a graph showing the absorption spectrum measured at intervals of 5 seconds during the process of isomerization from TA-4a dispersed in PMMA to TA-4b, and FIG. 13 is a graph showing the decay curve of the maximum absorption of PMMA in which Ta-4a was dispersed. As can be understood from this graph, the half-life at room temperature was 6.7 seconds. FIGS. 14(a) through 14(d) are pictures showing PMMA in which TA-4a was dispersed, taken (a) before an ultraviolet irradiation, (b) immediately after the ultraviolet irradiation, (c) 10 seconds and (d) 30 seconds after the ultraviolet irradiation. The PMMA, which was transparent before the ultraviolet irradiation as in FIG. 14(a), became colored immediately after the ultraviolet irradiation, as in FIG. 14(b). However, 10 seconds later, it became considerably faded (i.e. isomerized), as in FIG. 14(c). After 30 seconds, it was colorless, as in FIG. 14(d).

These results demonstrate that the absorbance will be halved about five seconds from the ultraviolet irradiation. Then, the compound will be approximately colorless after 10 seconds and completely colorless after 15 seconds. Thus, the photochromic compound according to the present example has been proven to be optically colorable and quick to be thermally faded even if it is dispersed into a polymer.

As explained thus far, the photochromic compound according to the present invention is quick to be thermally faded and easy to be dispersed into plastic macromolecular materials. An optical functional material produced by dispersing the photochromic compound according to the present invention into a plastic material will be colored when it is irradiated with visible light and quickly faded when it is under dark conditions. Such materials are suitable for sunglasses, goggles, visors, cosmetic, clothing, umbrella and other products.

It should be noted that the photochromic compounds described in the previous example presents only some specific forms of the present invention. It is possible to change, modify or expand the example within the spirit and scope of the present invention.

What is claimed is:

1. A photochromic compound expressed by a following general formula (I):

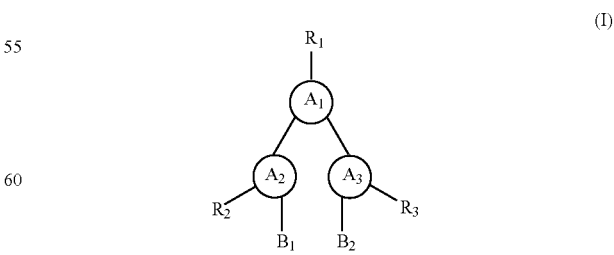

where:
each of $A_1$, $A_2$ and $A_3$ is a five-member ring forming a 6π-electron system, the three rings being identical, partially identical or totally different from each other, and each ring may have a substituent;

$B_1$ and $B_2$ are functional groups identical to or different from each other, each group having an atomic number of five or larger, including a ring compound, and $B_1$ is bonded to a 2-carbon of $A_2$, and $B_2$ is bonded to a 2-carbon of $A_3$; and $R_1$, $R_2$ and $R_3$ are substituents identical to or different from each other, wherein each of $R_2$ and $R_3$ in the general formula (I) is selected from phenylethynyl, thiophene, phenylenevinylene and thienylenevinylene.

2. A photochromic compound expressed by a following general formula (I):

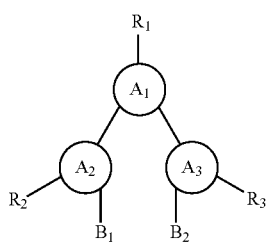

(I)

where:
each of $A_1$, $A_2$ and $A_3$ is a five-member ring forming a 6π-electron system, the three rings being identical, partially identical or totally different from each other, and each ring may have a substituent;

$B_1$ and $B_2$ are functional groups identical to or different from each other, each group having an atomic number of five or larger, including a ring compound, and $B_1$ is bonded to a 2-carbon of $A_2$, and $B_2$ is bonded to a 2-carbon of $A_3$; and $R_1$, $R_2$ and $R_3$ are substituents identical to or different from each other, wherein, in the general formula (I):

each of $A_1$, $A_2$ and $A_3$ in the general formula (I) is selected from thiazole, thiophene, pyrrole, indole, oxazole, imidazole and imidazolium;

each of $B_1$ and $B_2$ is selected from methyl, phenylethynyl, thiophene, phenylenevinylene and thienylenevinylene; and each of $R_2$ and $R_3$ is selected from phenylethynyl, thiophene, phenylenevinylene and thienylenevinylene.

3. A photochromic compound expressed by a following general formula (I):

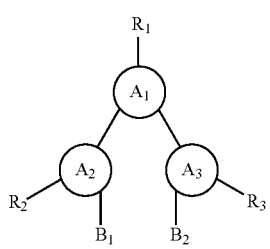

(I)

where:
each of $A_1$, $A_2$ and $A_3$ is a five-member ring forming a 6π-electron system, the three rings being identical, partially identical or totally different from each other, and each ring may have a substituent;

$B_1$ and $B_2$ are functional groups identical to or different from each other, each group having an atomic number of five or larger, including a ring compound, and $B_1$ is bonded to a 2-carbon of $A_2$, and $B_2$ is bonded to a 2-carbon of $A_3$; and $R_1$, $R_2$ and $R_3$ are substituents identical to or different from each other, wherein, in the general formula (I), $A_1$ is thiazole, $A_2$ and $A_3$ are thiophene, and $B_1$ and $B_2$ are phenylethynyl.

4. A photochromic compound expressed by a following structural formula:

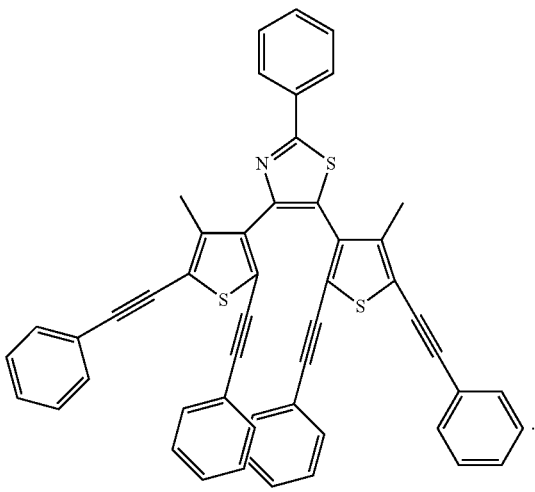

5. An optical functional material made of a plastic material in which a photochromic compound is dispersed, wherein the photochromic compound is expressed by a following general formula (I):

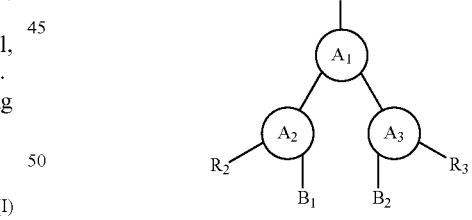

(I)

where:
each of $A_1$, $A_2$ and $A_3$ is a five-member ring forming a 6π-electron system, the three rings being identical, partially identical or totally different from each other, and each ring may have a substituent;

$B_1$ and $B_2$ are functional groups identical to or different from each other, each group having an atomic number of five or larger, including a ring compound, and bonded to a 2-carbon of each of $A_2$ and $A_3$, respectively; and $R_1$, $R_2$ and $R_3$ are substituents identical to or different from each other, wherein each of $R_2$ and $R_3$ in the general formula (I) is selected from phenylethynyl, thiophene, phenylenevinylene and thienylenevinylene.

6. An optical functional material made of a plastic material in which a photochromic compound is dispersed, wherein the photochromic compound is expressed by a following general formula (I):

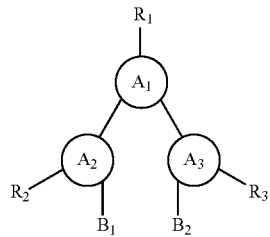
(I)

where:
- each of $A_1$, $A_2$ and $A_3$ is a five-member ring forming a 6π-electron system, the three rings being identical, partially identical or totally different from each other, and each ring may have a substituent;
- $B_1$ and $B_2$ are functional groups identical to or different from each other, each group having an atomic number of five or larger, including a ring compound, and bonded to a 2-carbon of each of $A_2$ and $A_3$, respectively; and
- $R_1$, $R_2$ and $R_3$ are substituents identical to or different from each other, wherein, in the general formula (I):
- each of $A_1$, $A_2$ and $A_3$ is selected from thiazole, thiophene, pyrrole, indole and imidazolium;
- each of $B_1$ and $B_2$ is selected from methyl, phenylethynyl, thiophene, phenylenevinylene and thienylenevinylene; and
- each of $R_2$ and $R_3$ is selected from phenylethynyl, thiophene, phenylenevinylene and thienylenevinylene.

7. An optical functional material made of a plastic material in which a photochromic compound is dispersed, wherein the photochromic compound is expressed by a following general formula (I):

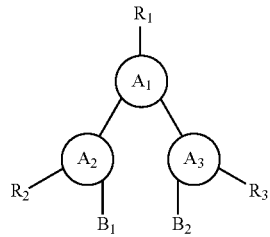
(I)

where:
- each of $A_1$, $A_2$ and $A_3$ is a five-member ring forming a 6π-electron system, the three rings being identical, partially identical or totally different from each other, and each ring may have a substituent;
- $B_1$ and $B_2$ are functional groups identical to or different from each other, each group having an atomic number of five or larger, including a ring compound, and bonded to a 2-carbon of each of $A_2$ and $A_3$, respectively; and
- $R_1$, $R_2$ and $R_3$ are substituents identical to or different from each other, wherein, in the general formula (I), $A_1$ is thiazole, $A_2$ and $A_3$ are thiophene, and $B_1$ and $B_2$ are phenylethynyl.

8. An optical functional material made of a plastic material in which a photochromic compound is dispersed, wherein the photochromic compound is expressed by a following structural formula:

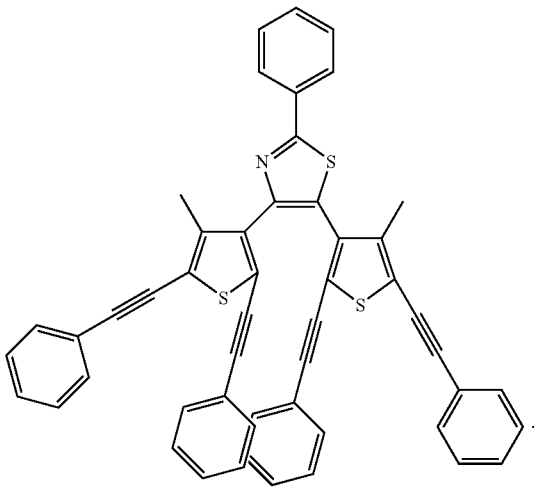

* * * * *